(12) United States Patent
Maxia

(10) Patent No.: US 10,034,856 B2
(45) Date of Patent: Jul. 31, 2018

(54) USE OF N-ACETYL-5-METHOXYTRYPTAMINE OR ANALOGUES THEREOF, FOR PROMOTING THE MECHANISM OF IMPLANTATION OF THE EMBRYO AND RELATED COMPOSITIONS AND CULTURE MEDIA

(71) Applicant: Ares Trading S.A., Aubonne (CH)

(72) Inventor: Nicoletta Maxia, Torre Delle Stelle (IT)

(73) Assignee: Ares Trading S.A., Aubonne (CH)

( * ) Notice: Subject to any disclaimer, the term of this patent is extended or adjusted under 35 U.S.C. 154(b) by 0 days.

(21) Appl. No.: 14/403,920

(22) PCT Filed: May 27, 2013

(86) PCT No.: PCT/EP2013/060872
§ 371 (c)(1),
(2) Date: Nov. 25, 2014

(87) PCT Pub. No.: WO2013/178587
PCT Pub. Date: Dec. 5, 2013

(65) Prior Publication Data
US 2015/0150847 A1    Jun. 4, 2015

(30) Foreign Application Priority Data
May 28, 2012 (IT) .............................. MI2012A0913

(51) Int. Cl.
| | |
|---|---|
| *A61K 31/4045* | (2006.01) |
| *A61K 9/00* | (2006.01) |
| *A61K 31/165* | (2006.01) |
| *C12N 5/071* | (2010.01) |
| *A61B 17/435* | (2006.01) |
| *A61B 17/42* | (2006.01) |

(52) U.S. Cl.
CPC ........ *A61K 31/4045* (2013.01); *A61B 17/435* (2013.01); *A61K 9/0034* (2013.01); *A61K 9/0039* (2013.01); *A61K 31/165* (2013.01); *C12N 5/0682* (2013.01); *A61B 2017/4216* (2013.01); *C12N 2501/825* (2013.01)

(58) Field of Classification Search
CPC .............. A61K 31/4045; A61K 9/0034; A61K 9/0039; A61K 31/165; C12N 5/0682; C12N 2501/825; A61B 17/435; A61B 2017/4216
See application file for complete search history.

(56) References Cited

U.S. PATENT DOCUMENTS

2008/0085556 A1    4/2008  Graefing et al.
2011/0020436 A1*   1/2011  Guilford .............. A61K 9/0014
                                                424/450

FOREIGN PATENT DOCUMENTS

| CN | 102250832 A | * 11/2011 |
|---|---|---|
| WO | 9622806 A1 | 1/1996 |
| WO | 9828007 A1 | 7/1998 |
| WO | 2007134077 A1 | 11/2007 |
| WO | 2008128095 A1 | 10/2008 |

OTHER PUBLICATIONS

Fischer et al (Skin Pharmacology and Physiology (2004), 17(4), 190-194).*
Choi, Anti-Apoptotic Effect of Melatonin on Preimplantation Development of Porcine Parthenogenetic Embryos, Molecular Reproduction and Development, 2008, pp. 1127-1135, vol. 75, published online Mar. 6, 2008 in Wiley InterScience (www.interscience.wiley.com).
Ishizuka, The effect of melatonin on in vitro fertilization and embryo development in mice, J. Pineal Res., 2000, pp. 48-51, vol. 28, printed in Ireland.
International Search Report for PCT/EP2013/060872, mailed by the European Patent Office dated Oct. 10, 2013.
Rodriguez-Osorio, Melatonin increases cleavage rate of porcine preimplantation embryos in vitro, J. Pineal Res., 2007, pp. 283-288, vol. 43.
Unfer, Effect of supplementation with myo-inositol plus melatonin on oocyte quality in women who failed to conceive in previous in vitro fertilization cycles for poor oocyte quality: a prospective, longitudinal, cohort study, Gynecological Endocrinology, Nov. 2011, pp. 857-861, vol. 27(11).
Abecia, The Effect of Melatonin on the Secretion of Progesterone in Sheep and on the Development of Ovine Embryos In Vitro, Veterinary Research Communications, 2002, pp. 151-158, vol. 26, published by Kluwer Academic Publishers in 2002 in the Netherlands.
Luck M R Et al, Melatonin directly stimulating secretion of progesterone of human granulosa cells, Acta Endocr, 1985 108:91, China.
Luck M R Et al, Melatonin directly stimulating secretion of progesterone of human granulosa cells, Acta Endocr, 1985 108:91, English translation.
Song, Research progress on traditional Chinese medicine (TCM) improving endometrial receptivity, Information on Traditional Chinese Medicine, 2011, vol. 28, No. 6, China.
Song, Research progress on traditional Chinese medicine (TCM) improving endometrial receptivity, Information on Traditional Chinese Medicine, 2011, vol. 28, No. 6, English translation.
Dair et al., Effects of melatonin on the endometrial morphology and embryo implantation in rats, Fertility and Sterility, May 2008, pp. 1299-1305, vol. 89, Suppl. 3, published by Elsevier Inc.
T. W. Fisher et al., "Percutaneous penetration of topically applied melatonin in a cream and an alcoholic solution", Skin Pharmacology and Physiology, 2004, pp. 190-194, vol. 17.

* cited by examiner

*Primary Examiner* — Sudhakar Katakam
(74) *Attorney, Agent, or Firm* — David A. Giordano; Giordano Law LLC

(57) ABSTRACT

The present invention refers to the use of N-acetyl-5-methoxytryptamine (melatonin) and/or an analog thereof, for use in the medical or veterinary field in the assisted reproduction for promoting the mechanism of implantation of the embryo, and in particular for the prevention of implantation failure into the uterus, by topical administration of an effective amount in a mammalian subject female in need of such treatment, and related compositions, culture media and medical devices.

6 Claims, 4 Drawing Sheets

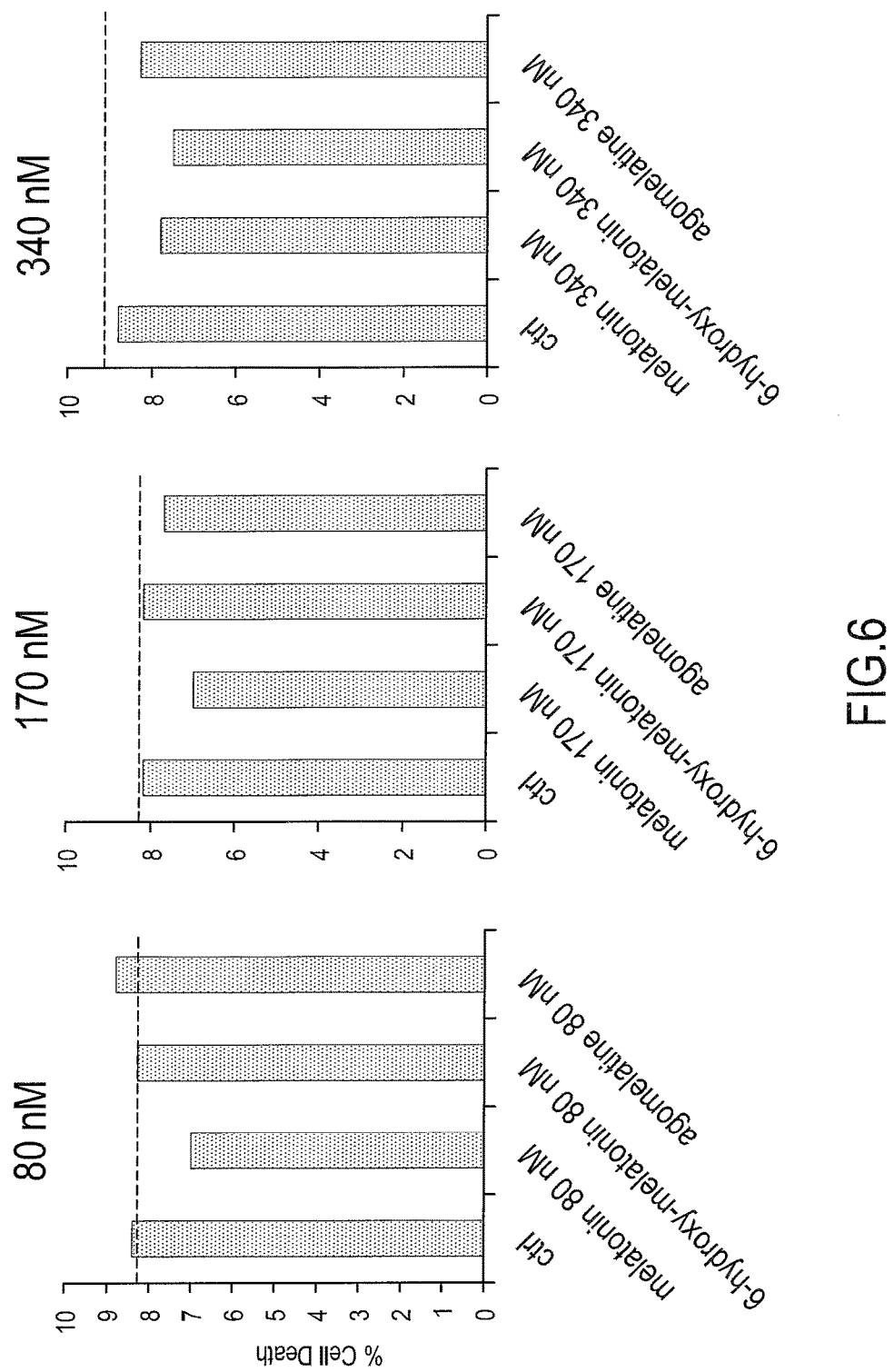

USE OF N-ACETYL-5-METHOXYTRYPTAMINE OR ANALOGUES THEREOF, FOR PROMOTING THE MECHANISM OF IMPLANTATION OF THE EMBRYO AND RELATED COMPOSITIONS AND CULTURE MEDIA

The present invention relates to the use of N-acetyl-5-methoxytryptamine (melatonin) and/or an analogue thereof, for use in the medical or veterinary field in the assisted reproduction for promoting the mechanism of implantation of the embryo, and in particular for the prevention of implantation failure into the uterus, by topical administration of an effective amount in a mammalian subject female in need of such treatment, and related compositions, culture media and medical devices.

The implantation of the human embryo into the uterus is a complex mechanism, which involves both the embryo, and the endometrial epithelium. The phases of apposition, adhesion and invasion involves a multiplicity of molecules, which play an unique role in the process, the molecular dialogue between the conceived and the endometrium implies interactions among cells, and between cells and biochemical factors.

These mechanisms, if suitably expressed or inhibited, are of help to determine the receptivity or non-receptivity state of the endometrium versus the embryo.

The state of endometrial receptivity or non-receptivity, although it is a largely shared concept, is clinically hard to be defined: the histological normality of the endometrium does not necessarily imply a functional normality; on the other side, the time and space expression of particular endometrial structures, named pinopodes, is strongly indicative of the receptivity state itself.

The implantation is a complex sequence of signals which are crucial for setting up pregnancy; it is supposed that a great number of molecular mediators under the influence of ovarian signals are involved in the embryo-endometrial interaction. These mediators comprise a wide range of molecules like hormones, cytokines, growth factors, lipids, adhesion molecules and else (1).

Failure in the implantation in the technologies of medically assisted reproduction (MAR) still remains an unsettled problem and it is considered one of the main reasons of infertility in healthy women. Considering then that the percentage of implantation of the techniques of MAR is of about 25%, the inadequate uterine receptivity is deemed as being responsible for about two thirds of all failures (for one third the embryo is considered as being responsible) (2).

The endometrium is receptive of the invasion of blastocyst for a range of a limited time and defined as "window of implantation". The "dialogue" for the synchronization between "ovulation-first phases of embryonic growth—cell modifications of endometrial epithelium for the implantation" is hold by a series of hormonal and biochemical messengers.

During the "implantation window", the endometrial epithelium expresses, through hormonal and biochemical control, some structures named pinopodes, capable to allow adhesion and invasion of blastocyst. The implantation window would be characterized, according to studies of electron microscopy (3) by the maximum expressivity of pinopodes.

The formation of pinopodes is considered as a specific marker of the endometrial receptivity, they appear about one week after ovulation, but their complete expression changes from patient to patient and seems to be maintained for only one day (4).

The expression of pinopodes is directly proportional to the increase of plasmatic levels of progesterone (5).

The concept of endometrial receptivity or "implantation window", connected to the expression of pinopodes, unanimously accepted by the scientific community, is for some decades subject-matter of study for the ones who face the problems related to assisted reproduction.

In summary: progesterone, the pro-gestation hormone, is the main mediator and around it rotate a plurality of other mediators which may promote the implantation occurrence.

From the aforesaid it comes out how the problem of obtaining pregnancy through techniques of assisted reproduction is mostly ascribable to the short knowledge of the implantation phenomenon.

It appears thus clear, also in view of the numerous legislative restrictions in the field of assisted reproduction, the necessity to optimize the phase of implantation.

The authors of the present invention have now found that one of the mediators capable to have a key role along with progesterone in the expression of pinopodes, with much positive effects for the embryonic nesting is N-acetyl-5-methoxy tryptamine (melatonin).

Melatonin is produced by the pineal, neuroendocrine gland controlled by light; darkness stimulates its synthesis and secretion.

The use of melatonin has no side effects or overdose problems, as well as no contraindication (6) is reported in literature.

Many are the advantages already known and associated with the use of melatonin also in different processes, which may positively interfere with the implantation. In this respect, it exists moreover an inversely proportional correlation with the risk of carcinoma of the endometrium and the serum levels of melatonin with ascertained protective action.

It has been proved by some authors (7) that melatonin inhibits proliferation of atypical endometrial cells, defined as Ishikawa, responsible for carcinoma of the endometrium. Through experiments with radioligands and antagonists of melatonin such as luzindole, the results of the group of researchers have proved that the inhibition effect is produced by melatonin through the MT2 receptors present in the membranes of the proliferative cells of Ishikawa.

Another determinant aspect to consider is the menopause period, during which melatonin diminishes its production and, indeed, during such a period the risk of endometrial carcinoma is higher.

For example, in vitro and in vivo (6, 8) studies have shown a strong antioxidant action of melatonin, said action being higher than that of mannitol, of glutathione and vitamin E in the protection from oxidative damage due to hydroxyl toxic radicals and to other catabolic cell products deriving from variations in the degenerative or proliferative metabolism and from/for lipid oxidation.

Melatonin (9-10) has moreover important anti estrogenic properties and stimulates production of progesterone which is in antithesis with the action of estrogens themselves (high levels of estrogens associate with a worst result in the techniques of assisted reproduction) (11).

In this regard, it is pointed out that super-ovulation through gonadotropins induced in MAR cycles, determines a hyperestrogenization with increase of endometrial hyperplasia, a significant risk factor for endometrial carcinoma as above mentioned.

Some authors (12) affirm that it exists a synergism between human chorionic gonadotropins (hCG) and melatonin: indeed, melatonin increases, by increasing inter alia the production of progesterone (both in vivo and in vitro), 6-7 days after the ovulatory peak of hCG.

In this regard it is highlighted how the post-ovulatory peak of melatonin perfectly coincides with the endometrial implantation window and with the formation of blastocyst (the step of embryonic growth in which the nesting into the uterus occurs). The positive correlation between melatonin and progesterone and the negative correlation between melatonin and estradiol would be enhanced by hCG: indeed, in the absence of the latter, melatonin has a very weak effect on production of progesterone.

An object of the present invention is N-acetyl-5-methoxy tryptamine or an analogue thereof, for use in the medical or veterinary field in assisted reproduction for the prevention of implantation failure into the uterus by topical administration of an effective amount in a mammalian subject female in need of such treatment.

Preferably, said analogue of N-acetyl-5-methoxy tryptamine is selected from agomelatine, 6-hydroxymelatonin, serotonin, 5 hydroxytryptophan or their derivatives.

In a preferred embodiment of the invention the mammalian subject female is a woman suffering from infertility or polyabortion.

According to a further preferred embodiment, the topical administration of N-acetyl-5-methoxy tryptamine or an analogue thereof, preferably of N-acetyl-5-methoxy tryptamine, takes place through endometrial irrigation or uterine washing or endometrial washing.

Still according to a further preferred embodiment of the invention, said topical administration occurs in a single administration at the time of oocyte retrieval.

Preferably, said active principle is present in a concentration ranging from $4\times10^{-9}$ g/ml to $25\times10^{-9}$ g/ml, still more preferably greater than or equal to $10\times10^{-9}$ g/ml.

In an alternative embodiment, it is possible the concurrent use with a systemic therapy based on N-acetyl-5-methoxy tryptamine, hCG or progesterone, or a combination thereof, from the day of oocyte retrieval.

In alternative preferred embodiments of the present invention, the techniques of assisted reproduction are selected from the group consisting in basic or of I level techniques, simple and not much invasive as targeted intercourse or intrauterine artificial insemination and II or III level techniques, which are more complex and invasive selected from in vitro fertilization (IVF), in vitro fertilization and embryo transfer (FIVET), intracytoplasmic sperm injection (ICSI), intracyitoplasmic morphologically selected sperm injection (IMSI) and Tese-Tesa techniques (Testicular Sperm Aspiration-Extraction). Artificial fertilization stands mainly for the technique of intrauterine insemination (IUI), which is a technique of medically assisted reproduction, wherein the seminal fluid is introduced inside the uterine cavity. It may be suggested in all those cases of incompatibility between cervical mucus and seminal fluid, in that it allows to go beyond the cervical length and insert spermatozoa directly into the uterus. It is moreover used in case of unexplained sterility, of male infertility of light or moderate degree, in cases of reiterated failures in the induction of pregnancy with stimulation of ovulation and targeted intercourse and in cases of sexual disorders which do not allow a complete sexual intercourse.

In vitro fertilization and embryo transfer (FIVET) is a MAR technique wherein human gametes are withdrawn, placed under culture and, after fertilization and production of one or more embryos, these are transferred into the uterus. This technique is suggested in cases of:

Acquired or congenital tubal pathology;
male infertility of moderate degree;
endometriosis of III or IV level;
unexplained infertility;
cryo-preserved semen in relation to the seminal quality, subsequent to thawing;
failing of the therapeutic procedure of I level techniques.

After ovarian stimulation, oocytes retrieval (PICK-UP) is carried out via transvaginal operation, under echographic control, in local anaesthesia and/or deep sedation, a preparation of the sperm is effected and the oocytes to be fertilized are selected. Next, the extracorporeal culture of gametes is prepared and after verifying the occurred fertilization, the transfer into the uterus of a definite number of embryos is performed.

The intracytoplasmic sperm micro-injection (ICSI) uses various steps of the FIVET. Also in this case the fertilization is extracorporeal, but it takes place with the injection of a single spermatozoon inside the cytoplasm of the oocyte. Then, after the occurred fertilization, the embryos are transferred into the uterus.

This technique is suggested in cases of:
male infertility of severe degree;
occlusive and secretive azoospermia (testicular spermatozoa or epididymis);
failed or reduced fertilization in previous cycles of in vitro fertilization (IVF);
thawed oocytes;
reduced number of oocytes;
cryo-preserved semen in relation to the seminal quality subsequent to thawing.

Also this technique can be carried out under spontaneous cycle or through induction of multiple follicular growth and after having stimulated the ovary to produce more follicles and so having obtained more oocytes, oocyte retrieval (PICK-UP) is carried out via transvaginal operation. Contemporaneously to PICK UP, preparation of the sperm is effected. In case of azoospermia, the techniques used for withdrawal of spermatozoa are: Testicular Sperm Percutaneous Aspiration (TESA), Testicular Sperm Extraction (TESE), Microchirurgical Epididymal Sperm Aspiration (MESA), Percutaneous Epididymal Sperm Aspiration (PESA).

Subsequently, the preparation of the oocyte and the insemination of oocytes through intracytoplasmic microinjection technique of a single spermatozoon takes place. After verifying the occurred fertilization of each oocyte, the embryos are transferred into the uterus.

It is a further object of the present invention a composition suitable for topical administration comprising N-acetyl-5-methoxytryptamine or an analogue thereof, or their combination as active ingredient, in an effective amount in a mammalian subject female in need of such treatment, along with one or more physiologically acceptable excipients or adjuvants, for use in the medical or veterinary field in the assisted reproduction for the prevention of implantation failure into the uterus.

Preferably, said active ingredient is present in the composition in a concentration ranging from $4\times10^{-9}$ g/ml to $25\times10^{-9}$ g/ml, preferably greater than or equal to $10\times10^{-9}$ g/ml.

According to a preferred embodiment, the active ingredient in the above mentioned composition is formulated as endometrial/uterus irrigation/washing in a cell culture medium in a final concentration ranging from $4\times10^{-9}$ g/ml to $25\times10^{-9}$ g/ml, preferably greater than or equal to $10\times10^{-9}$ g/ml. Such a culture medium for blastocyst may preferably comprise the following components:
source of D-glucose;
Antibiotic, preferably gentamicin;
Human serum albumin;
Essential and non-essential amino acids, preferably L-taurine;
buffer salts preferably selected between:
Calcium salts: calcium lactate, calcium pantothenate;
Sodium salts: sodium chloride, sodium bicarbonate and sodium pyruvate;
Potassium salts: potassium chloride, potassium phosphate;
Magnesium salts: magnesium chloride, magnesium sulphate
and mixtures thereof;
Water;
and has a pH between 7.5 and 7.8.

According to a preferred embodiment said culture medium may be Sydney IVF® Blastocyst medium.

According to an alternative embodiment of the present invention, the active ingredient of the above mentioned composition is formulated as endometrial irrigation, endometrial washing or uterine washing in physiological solution with a final concentration ranging from $4 \times 10^{-9}$ g/ml to $25 \times 10^{-9}$ g/ml, preferably greater than or equal to $10 \times 10^{-9}$ g/ml.

In females, the procedure of washing of the uterine cavity has been commonly used with the main objective to set non-invasive prenatal diagnosis, innovative with respect to invasive traditional methods of amniocentesis and chorionic villus sampling [(13)(14)]. In recent years, such technique has been applied to evaluate the conditions of the uterine cavity before the transfer of the embryo in the cycles of assisted reproduction. The application of this procedure consists in the insertion into the uterus of a buffer solution with the aim at collecting uterine secretes and evaluate their organic and inorganic biological components. It has the purpose to identify possible markers, predictive of implantation success [(15)(16)(17)(18)].

Still preferably, said composition suitable for topical administration through uterine washing further comprises essential and non-essential amino acids, and buffer salts. Preferably said buffer salts are salts of calcium, sodium, potassium and magnesium, and mixtures thereof. The use of buffer salts and amino acids is provided for producing a formulation with a pH comprised between 7 and 8 (preferably between 7.5-7.8), to replicate the micro-environment suitable for the embryo (and similar to that of culture media in which the embryo grows before the transfer into the uterus).

According to an alternative embodiment, the compositions of the invention may be formulated as gel suitable for uterine administration, more precisely for in situ administration in the uterine cavity, preferably with a medical device being an intrauterine "T shaped" device. It is also possible to foresee controlled release gel formulations for mucosal administration.

Considering that the uterine washing technique as above described revealed to be a non-invasive practice and that allows restoration of the uterine physiological conditions through mechanical removal of secretes, which may alter the implantation conditions, the invention has as a further object a medical device for uterine washing comprising a sterile container pre-filled or to be filled with a composition as above defined.

More precisely, the device according to the present invention can be filled at the moment of use with a sterile solution suitable for the uterine or endometrial washing supplemented with the active principle melatonine or analogue thereof according to the present invention already formed or it can be filled with such sterile solution supplemented just at the moment of use with the active principle.

According to a preferred embodiment the sterile container is disposable. More preferably the sterile container (preferably a disposable sterile container) is pre-filled with physiological solution supplemented with melatonin (in a concentration ranging from $4 \times 10^{-9}$ g/ml to $25 \times 10^{-9}$ g/ml, preferably greater than or equal to $10 \times 10^{-9}$ g/ml), buffer salts and amino acids such as to produce a formulation with pH comprised between 7-8, preferably between 7.5 and 7.8.

The uterine washing shall be performed with the aid of a catheter after pick-up with echographic guide. The next embryos transfer or implantation shall take place averagely three days after the washing (2-5 days).

Therefore, according to preferred embodiments of the invention the medical device according to the invention may further comprise a sterile flexible catheter, preferably with a single terminal hole.

The sterility of the medical device components is achieved preferably through sterile filling or final sterilization, such as heating treatment or through gamma rays treatment.

In addition, the medical device can be accompanied by instructions for use in the various MAR techniques.

The purpose of the medical device is that of removing oxidant substances and possible secreted products in response to the stimulation preceding the MAR techniques and thus of restoring the physiological composition of the endometrial exudate. The objective is that of avoiding that such oxidizing substances and secreted products reduce the percentage of implantation in patients subjected to MAR. As above anticipated, the use of buffer salts and amino acids is provided for setting a pH comprised between 7-8, preferably between 7.5 and 7.8, for replicating the micro-environment suitable for the embryo. The addition of melatonin, additional to the effects shown within the present invention, exerts a very strong antioxidant effect and a safety action versus endometrial cells, of the oxidative damage due to toxic radicals and other catabolic products.

Preferably, said disposable sterile container is selected from syringe, dispenser, cartridge for self-injection/pen.

According to particularly preferred embodiments of the invention the syringe is of the luer-lock type 3 ml made of polycarbonate or borosilicate glass. When a syringe of the luer-lock type is used, the intrauterine catheter possibly associated with the medical device according to the invention is provided with a luer lock female joint for coupling with the syringe.

Alternatively, if a self-injection system or a pen is used (insulin type) it can be used a glass cartridge 3 ml of borosilicate glass.

Still preferably said disposable sterile container is pre-filled with volume of 1.5 ml of washing solution containing:
$10 \times 10^{-9}$ g/ml (10 ng/ml) of melatonin
essential and non-essential amino acids
calcium salts
potassium salts
magnesium salts
a pH comprised between 7.5-7.8 and osmolarity comprised between 280-290 mOsm/kg.

The invention has also as an object the medical device as above illustrated for use in a single administration as endometrial washing at the moment of the oocyte retrieval in protocols of medical assisted reproduction.

The invention also refers to a cell culture medium in vitro or in vivo, comprising the following components:
  source of D-glucose;
  Antibiotic, preferably gentamicin;
  Human serum albumin;
  Essential and non-essential amino acids, preferably L-taurine,
  Calcium salts: calcium lactate, calcium pantothenate;
  Sodium salts: sodium chloride, sodium bicarbonate and sodium pyruvate;
  Potassium salts: potassium chloride, potassium phosphate;
  Salts of magnesium: magnesium chloride, magnesium sulfate;
  Water;
characterized in that it further comprises N-acetyl-5-methoxy tryptamine or an analogue thereof, or their combination, wherein said active ingredient is present in a concentration ranging from $4 \times 10^{-9}$ g/ml to $25 \times 10^{-9}$ g/ml, preferably greater than or equal to $10 \times 10^{-9}$ g/ml.

It stands for a further object of the present invention a cell culture medium for the expansion of pinopodes and the achievement of an in vitro model study.

Such a cell culture medium can be used also for embryonic cultures, by achieving for example a culture medium which is used for transferring the embryo into the uterus, said medium being thus inserted into the uterus.

Particularly advantageous aspects of use according to the present invention are connected to the proposed route of topical administration, which does not compromise the MAR treatment cycle, being such a route much less invasive than endometrial biopsy, already applied to women subjected to a cycle of MAR (13).

At last, thanks to the properties of synthesis inhibition by side of prostaglandins (14), which are typical of melatonin, this washing reduces uterine contractions and further promotes implantation.

The present invention will be now described in an illustrative manner, but not limitative, according to two preferred embodiments, with particular reference to the annexed figures, wherein.

Figure 1:
FIG. 1 illustrates the endometrium before treatment through the composition according to the present invention, therefore in the absence of pinopodes.
Figure 2:
FIG. 2 illustrates the endometrium 1/2 days after treatment through the composition according to the present invention: the formation of pinopodes starts to come into sight.
Figure 3:
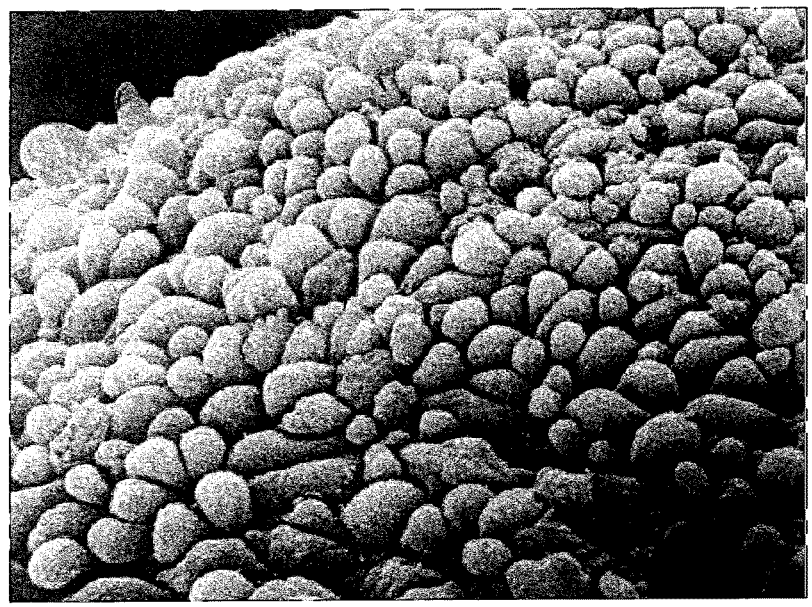
FIG. 3 illustrates the endometrium 3/4 days after treatment through the composition according to the present invention: maximum growth of pinopodes.
Figure 4:
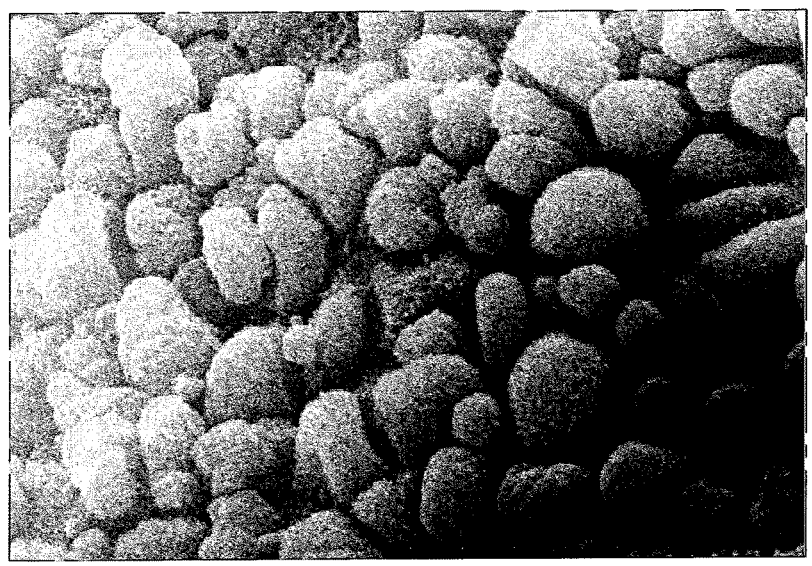
FIG. 4 illustrates the endometrium 5/6 days after treatment through the composition according to the present invention: it starts cleavage of pinopodes, which appear to be irregular (cell apoptosis).
Figure 5:
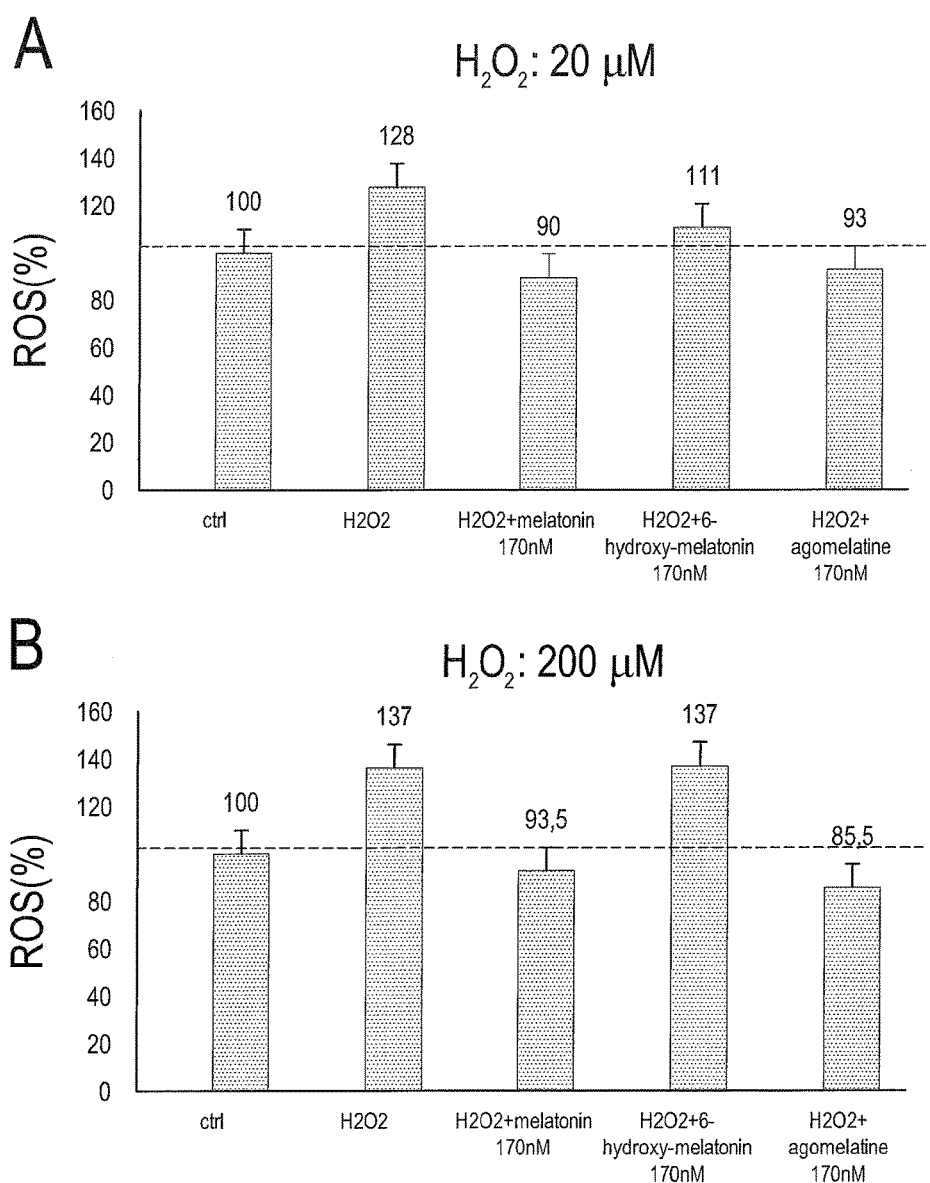

FIG. 5 shows the results of the FACS analysis (fluorescence intensity measurement) of the antioxidant activity of melatonin, agomelatine and 6-hydroxymelatonin (170 nM corresponding to $40 \times 10^{-9}$ g/ml) carried out at $H_2O_2$ concentrations of 20 μM and 200 μM;

FIG. 6 shows the results of apoptosis assay (% cell death) carried out at different concentrations (80 nM, 170 nM, 340 nM; corresponding respectively to $18 \times 10^{-9}$ g/ml, $40 \times 10^{-9}$ g/ml, $80 \times 10^{-9}$ g/ml) of melatonin, agomelatine and 6-hydroxymelatonin.

Merely for example, but not limitative of the present invention, hereinafter are reported the comparative studies carried out (in vitro and in vivo) by the authors of the present invention to evaluate the percentage increase of human embryonic implantation in MAR techniques through the use of melatonin in different solutions.

EXAMPLE 1: IN VIVO STUDIES

Materials and Methods
Solutions of Melatonin Used for Endometrial Washings
The melatonin (or N-acetyl-5-methoxy tryptamine; CAS Number 73-31-4) used has been obtained at Farmalabor as product in form of powder with title ≥99%.

Two clinical trials have been carried out providing the administration of melatonin (concentration $10 \times 10^{-9}$ g/ml) through endometrial washing in:
1) culture medium Sydney IVF® Blastocyst medium (Clinical trial 1) supplied by Cook Ireland Ltd (Catalogue Number G20722 and G20929). Said culture medium is normally used to improve cleavage, differentiation and expansion in vitro of blastocyst. The medium contains D-glucose, all the 20 essential L-amino acids, L-taurine, Gentamicin, human serum albumin, calcium lactate, calcium pantothenate; sodium chloride, sodium bicarbonate and sodium pyruvate; potassium chloride, potassium phosphate; magnesium chloride, magnesium sulfate; purified water.
Further characteristics of the culture medium:
pH: 7.5-7.8 (use of bicarbonate buffer)
Osmolarity: 280-290 mOsm/kg
Endotoxins: <0.4 EU/ml
MEA: ≥80%
2) Physiological Solution (Clinical Trial 2)

Statistical Analysis:
It has been carried out a statistical analysis (IM-PRUN.TXT) of linear regression with more variables.

Statistical Methods:
The role of the number of implanted embryos, of their quality and of the washing process with the solution containing melatonin in the increasing of the chance of pregnancy has been computed by means of non-conditional logistic regression, by adjustment according to the mother's age.

The ratio between the chance of pregnancy associated with each procedure (number of embryos, their quality and application of the washing process with saline solution or Blastocyst medium containing melatonin) and the chance of pregnancy with reference respectively to the lower category of number of embryos (one), to the quality less than optimal of implanted embryos, or to the absence of the washing process, has been defined as Odds Ratio (OR), and it has been computed through non-conditional logistic regression, by adjustment according to the mother's age.

In the logistic regression, OR corresponds to the antilogarithm on a natural basis of the regression coefficient β associated with each covariate in the regression model.

The value thus calculated expresses therefore the advantage obtained through each procedure, irrespective of the other conditions.

The two-tailed confidence intervals at 95% (IF95%) of the OR have been calculated through the formula of Wald ($e^{\beta \pm (z_{\alpha/2} * se_\beta)}$).

Sterility Controls (Culture Medium)
To carry out the sterility controls of the culture medium supplemented with melatonin it has been used the BACT/ALERT 3D-60 device (BIOMERIEUX). The bottles of Bact/ALERT culture are applied to systems of microbial detection in qualitative procedures for recovering and detecting optional anaerobic and aerobic (bacteria) in the blood and other fluids normally sterile as the Blastocyst medium used in the present experimentation.

The Bact/ALERT system of microbial detection is used to determine whether microorganisms are present in the samples of blood or of other fluids normally sterile as the blastocyst medium used in our invention, with suspected bacteremia. The Bact/ALERT system and the culture bottles offer a system of microbial detection and a culture medium with environmental and nutritional conditions suitable for microorganisms commonly present in blood infections and other fluids normally sterile.

The inoculated bottles (from a minimum of 5 ml to a maximum of 10 ml of sample at issue) are incubated in the device, where they are subjected to continuous monitoring in order to detect a possible growth of microorganisms in the Bact/ALERT bottles.

The Bact/ALERT system of microbial detection uses a colorimetric sensor and reflected light for monitoring the presence and the production of carbon dioxide ($CO_2$) dissolved in the culture medium.

The microorganisms possibly present in the sample metabolize the substrates in the culture medium producing carbon dioxide. The production of $CO_2$ determined by the growth of microorganisms induces the gas permeable green-blue sensor present on the bottom of each culture bottle to take a yellow colour.

The lighter colour indicates an increase of the units of monitoring reflectance of the system.

The reflectance of the bottle is monitored and traced by the device every 10 minutes.

The culture bottles are established as being positive or negative by the managing software of Bact/ALERT systems of microbial detection after 6 days of incubation.

No intervention is necessary up to the moment in which the Bact/ALERT device alerts that a culture bottle is positive or negative.

Before carrying out any endometrial irrigation culture tests have been carried out for testing sterility in 2-4-6 days and once the negative culture was found it was used into the uterus.

Criteria of Inclusion

Restricted criteria of inclusion have been used for selecting the patient population involved in the studies:
3) age ≥20 and <44 years
4) body mass index (BMI) ≥20 and ≤28 kg/m²
5) Basal FSH≤19 UI/l
6) Male and female factors Patients The patients involved in all the two clinical studies, after collecting informed consent, have been subjected to assisted reproduction.

In this first two-arms randomized multi-centre clinical study (control and study group) involved about 430 patients/arm.

The patients undergoing assisted fertilization have been randomized the day of oocyte retrieval in three groups:
Group A: 430 patients to be subjected to endometrial irrigation with 1.5 ml of physiological solution (controls).
Group B: 436 patients to be subjected to endometrial irrigation with a solution of 1.5 ml of culture medium supplemented with final concentration of melatonin ($10 \times 10^{-9}$ g/ml).
Group C: patients not subjected to endometrial irrigation.

The study has been carried out involving patients in several private centers specialized in MAR, such as the Center of BRA, the Promea Center of Torino and Cagliari, the Genera Center of Perugia and the polyclinic Public Center of Bari. To these centres it has been sent the culture medium supplemented with melatonin after having been subjected to sterility tests to carry out the following protocol of treatment.

After in vivo enrolling for assisted fertilization by endometrial irrigation with known concentration (final concentration of $10 \times 10^{-9}$ g/ml) of melatonin at the time of oocyte retrieval, patients were subjected to related ultrasound-guided visualization of the diameter of liquid stratum created on the bottom of the uterus.

The second clinical study with a single prospective centre involved 64 patients in the group of control and 92 patients in the group of study.

In said study melatonin has been administered in sterile physiological solution, through endometrial washing inside the uterine cavity of patients, following to oocyte retrieval.

Endometrial Washing

Briefly, the treatment consists in endometrial irrigation inside the uterine cavity without any cell in co-culture, using the physiological solution or the culture medium admixed with melatonin with final concentration of $10 \times 10^{-9}$ g/ml (preceding studies had been effected with one third and the half of the final concentration then maintained without giving the same results—not shown data).

After oocyte retrieval, (the time correspondent to the ovulation after the administration of hCG in the protocols of MAR) after having controlled the vaginal homeostasis, it has been jointed a sterile syringe from 2.5 ml to a single-lumen intrauterine catheter with apical opening and the culture medium (Blastocyst medium) or the physiological solution has been suctioned, modified through addition of melatonin up to a volume of 1.5 ml.

In the case of the physiological solution, the catheter can be pre-filled with physiological solution supplemented with melatonin.

The catheter has been introduced in the internal uterine orifice with the same steps through which the operator carries out the conventional embryo-transfer (ET).

Then, it has been slowly injected the saline solution supplemented with melatonin or the modified medium and, at the end of irrigation, the thickness of the endocavitary liquid stratum has been measured by transabdominal echography (washing and echography must be simultaneous, the liquid stratum arrives at about 10 mm and then quickly disappears).

Results

Clinical Study 1

The multi-centre in vivo study involved 863 patients subjected to assisted fertilization and to endometrial irrigation (echographic measurements of the liquid stratum) with melatonin and 3-4 days after that, they have been subjected to embryonic transfer. For the latter, the CI (confidence interval or trust interval) has been calculated through statistical analysis (IMPRUN. TXT) of linear regression with more variables of 95%.

The univariate analysis shows that the implantation of 3 embryos implies a significant increase, equal to about 3 times (OR=2.8, IF 95% 1.7-4.4) the chance of pregnancy.

A number of two embryos does not appear instead to be sufficient to increase the chance of pregnancy (OR=1.0, IF 95% 1.7-4.4).

On the other hand, also the optimal quality of the implanted embryos seems to be an important factor in increasing the chance of pregnancy (OR=2.9, IF 95% 1.8-4.7). In the univariate analysis, the same rate of relevance appears to be associated with the use of the irrigation procedure (OR=2.2, IF 95% 1.6-2.9).

The multivariate analysis allows to control the independent effect of each variable, therefore totally irrespective of the effect of the other applied procedures and of the mother's age. In this case, the use of the washing procedure doubles the chance of success of pregnancy (OR=2.2, IF 95% 1.6-3.0).

A similar improvement appears to be associated with the implantation of three embryos, rather than the implantation of a single embryo (OR=2.1, IF 95% 1.2-3.7), and to the use of embryos of optimal quality (OR=1.9, IF 95% 1.1-3.3).

The use of all the three procedures as above reported seems to be therefore the best choice in the procedures of assisted fertilization.

In conclusion, the in vivo studies have proved that the irrigation or the washing with melatonin of endometrial cells allows to double the number of pregnancies with respect to the other two groups, which did not differentiated significantly.

Clinical Study 2

The single centre study involved 64 patients in the group of control and 92 patients in the group of study.

The patients have been subjected to assisted reproduction and to endometrial washing (echographic measurements of the liquid stratum) with melatonin in sterile saline solution, and 3-4 days after they have been subjected to embryonic transfer.

The primary endpoint of the study is the rate of clinical pregnancies (fetal heart) due to embryonic transfer (ET); the secondary endpoint is the rate of ongoing pregnancies and aborts.

The rate of clinical pregnancies resulted to be equal to 37% in the group of study vs 17.2% in the group of control, whereas the rate of ongoing pregnancies resulted to be equal to 32.6% in the group of study vs 14.1% in the group of control.

The results have been reported in the following Table 1.

TABLE 1

|  | CONTROL | | WASHING | |
| --- | --- | --- | --- | --- |
|  | No | (%) | No | (%) |
| No ET | 64 | | 92 | |
| Age (years ± SD) | 38.8 ± 1.2 | | 36 ± 4 | |
| No embryos transferred (Average ± SD) | 2.7 ± 1.1 | | 2.5 ± 1.08 | |
| No embryos Grade A (Average ± SD) | 1.5 ± 1 | | 1.3 ± 0.8 | |
| No embryos Grade B (Average ± SD) | 0.9 ± 0.7 | | 1.17 ± 0.8 | |
| No embryos Grade C (Average ± SD) | 0.2 ± 0.5 | | 0.1 ± 0.3 | |
| Day ET (Average ± SD) | 3.5 ± 0.5 | | 3.5 ± 1.2 | |
| BHCG Positive (on total of ET) | 12 | 18.8% | 41 | 44.6% |
| Clinical Pregnancy/ET | 11 | 17.2% | 34 | 37.0% |
| Ongoing Pregnancy/ET | 9 | 14.1% | 30 | 32.6% |
| Aborts | 1 | 9.1% | 4 | 11.8% |

The endometrial washing carried out with the various solutions containing melatonin, allows to double the rate of clinical pregnancies and ongoing pregnancies vs the group of control in the infertile female population.

The data seem to confirm that the removal of endometrial exudate using the physiological solution with melatonin can create a physiological endometrial environment and improve implantation success.

This allows to obtain a valid and innovative means for increasing the implantation rates in assisted reproduction technologies (ART).

EXAMPLE 2: IN VITRO STUDY

Materials and Methods

The melatonin and the culture medium used are the same as those used for the in vivo study.

Electron Microscopy (SEM)

It has been used a field emission at high resolution electron microscope, FE HITACHI S 4000 model, operating at 15-20 KW.

Preparation of Samples

Soon after retrieval from the patient, small pieces of endometrial tissue of about 1 mm in size have been placed in a fixing solution composed of paraformaldehyde 1% and glutaraldehyde 0.5% in buffer cacodylate 0.1 M pH 7.2 for 3 hours.

After this fixing the pieces are washed in PBS 20 min×3 times (1 hour total) and then the post fixing is carried out in a solution of osmium tetroxide 2% and potassium ferrocyanide 2.5%.

The preparation is kept in the dark for 3 hours to be then accurately washed rotating in PBS, with 4 replacements of 20 min each.

It follows dehydration of the samples of tissue with acetone in ascending succession with 3 replacements in 1 hour for each gradation 50%-70%-80%-90%-95% and 2 replacements with pure acetone.

At this stage it follows drying up to the critical point with liquid $CO_2$ in the apposite high-pressure device which substitutes acetone 10% with liquid $CO_2$, it is then slowly brought to the critical point temperature and $CO_2$ evaporates. At this point the samples of tissue are perfectly anhydrous and can be arranged on the trays of the electron microscope.

The samples are fixed through a special electrically conductive double sided adhesive and for their arrangement two very thin needles are used and the preparation is ready to be observed with scanning electron microscope (SEM).

Biological Samples

Under prior informed consent, they have been placed under culture fragments of endometrium withdrawn from patients subjected to diagnostic hysteroscopy.

For each patient, two parts have been set: one part of the tissue has been placed under culture through a conventional Blastocyst Medium void of melatonin, the other part through a conventional Blastocyst medium supplemented with melatonin.

Culture Set

In vitro culture of endometrium (withdrawn through hysteroscopy from patients subjected to assisted pre-fertilization controls) with melatonin for 3-6 days and correlated visualization of pinopodes through electron microscopy (SEM).

Results

In vitro studies have shown that the co-culture from 3 to 5 days of endometrial tissue in test-tube with permanent addition of melatonin, involves an unquestionable increase of pinopodes (under electron microscopy (SEM)), irrespective of the age of the patient and of the menstrual cycle phase in spontaneous cycles or manipulated through pharmacological stimulation of super-ovulation, with respect to the culture of control. Such pinopodes are structures which are defined as the most important implantation marker which for each woman (with a variability of 5 days, that is, a woman can menstruate after 26 days with short cycle or menstruate after 33 days) is of 48 hours. In fact, two thirds of success of becoming pregnant depends on the correct moment of implantation, the other third depends on the quality of the embryo.

The examination under the electron microscope SEM has shown that the addition of melatonin leads to a complete morphological expression of pinopodes as illustrated in FIGS. 1-4.

This outlines the importance of pinopodes during the implantation window and the increase of their expression induced in culture through mediums supplemented with melatonin.

EXAMPLE 3: STUDY ON THE EFFECTS OF MELATONIN AND ANALOGUES ON OXIDATION AND APOPTOSIS OF ENDOMETRIAL CELL LINE HEC-1-A

Tested Compounds

The analogues of melatonin which has been used for Comparison with melatonin (M5250), are agomelatine (A1362) and 6-hydroxy melatonin (H0627), all purchased from Sigma Aldrich.

They were used in different concentrations (i.e. 40 nM, 80 nM, 170 nM and 340 nM, corresponding respectively to $9.4 \times 10^{-9}$ g/ml, $18 \times 10^{-9}$ g/ml, $40 \times 10^{-9}$ g/ml and $80 \times 10^{-9}$ g/ml).

Cell Line

HEC-1A cells were obtained by ATCC and culture following instructions of the provider.

HEC-1-A is an epithelial stabilized cell line isolated by H. Kuramoto from adenocarcinoma patient (21), which provide a valuable model to study endometrial epithelial cell in vitro (22).

Antioxidant Activity Assay

The HEC-1-A cell line was cultured with 170 nM (40 ng/ml) of Melatonin, 6-hydroxy-melatonin and agomelatine and two different concentrations of $H_2O_2$ (20 and 200 mcg/ml).

Reactive Oxidative Substances (ROS) were measured by FACS as previously described by Italiano et al. (23) in two independent replicates.

Results

Melatonin and the two analogues asserted the same anti-oxidative effect, on the in-vitro cell line model, at the $H_2O_2$ concentration of 20 mcg/ml.

When the $H_2O_2$ concentration is increased up to 200 mcg/ml melatonin and agomelatine continued to protect cell line from oxidation, whereas the 6-hydroxy-melatonin does not. However, increasing the 6-hydroxy-melatonin dose up to 340 nM the anti-oxidative effect of this analogue is reached (data not shown).

Results are illustrated in the chart of FIG. 5.

These results are in line with data published by Duan et al. (24) on the anti-oxidative effect of melatonin in a different cell model and demonstrate that melatonin and analogues assayed have a similar effect at least when 20 mcg/ml of $H_2O_2$ is used on endometrial cell line.

Apoptosis Assay

The apoptosis (% cell death) of the endometrial cells is a physiological phenomenon generally observed at 10-20% rate during cell culture.

In order to determine if melatonin and its analogs induce cell death in this specific experimental context, we have treated the HEC-1-A cell line with 340 nM (80 ng/ml), 170 nM (40 ng/ml) and 80 nM (18.8 ng/ml) of melatonin, 6-hydroxy-melatonin and agomelatine, respectively, for 24 hours.

Apoptosis levels were assayed by Propidium Iodide staining and FACS analysis. Percentage of sub-G1 events is shown for one of two experiments performed.

Results

In all the concentrations tested, Melatonin exerts a protective effect on apoptosis. Agomelatin has a protective effect at 170 and 340 nM, while no effect on apoptosis is shown by 6-hydroxy-melatonin up to concentration of 170 nM. Results are shown in FIG. 6.

BIBLIOGRAPHY

1. Simon C, Martin J C, Pellicer A. Clin obst & gynaecol, 2000 14; (5) 127: 815-826.
2. Lédéé-Bataille N, Laprée-Delage G, Taupin J L, Dubanchet S, Frydman R, Chaouat G. Hum Reprod, 2002 Jan. 17; (1): 213-218.
3. Nardo L G, Sabatini L, Rai R, Nardo F. Eur J Obstet Gynecol Reprod Biol, 2002 Mar. 10; 101 (2): 104-8.
4. Nikas G, Makrigiannakis A. Ann N Y Acad Sci, 2003 November; 997: 120-3.
5. Stavreus-Evers A, Mandelin E, Koistinen R, Aghajanova L, Hovatta O, Seppala M. Fertil Steril, 2006 June; 85 (6): 1803-11. Erratum in: Fertil Steril. 2006 August; 86 (2): 498.
6. Brzezinski A. N Engl J Med, 1997 Jan. 16; 336 (3): 186-95.
7. Kobayashi Y, Itoh M T, Kondo H, Okuma Y, Sato S, Kanishi Y, Hamada N, Kiguchi K, Ishizuka B. J Pineal Res, 2003 September; 35 (2): 71-4.
8. Aydogan S, Yerer M B, Goktas A. Melatonin and nitric oxide. J Endocrinol Invest, 2006 March; 29 (3): 281-7.
9. Sandyk R, Anastasiadis P G, Anninos P A, Tsagas N. Int J Neurosci, 1992 February; 62 (3-4): 243-50.
10. Sandyk R, Anastasiadis P G, Anninos P A, Tsagas N. Int J Neurosci, 1992 January; 62 (1-2): 89-96.
11. Simón C, Garcia Velasco J J, Valbuena D, Peinado J A, Moreno C, Remohi J, Pellicer A. Fertil Steril, 1998 August; 70 (2): 234-9.
12. Tang P L, Chan T Y, Tang G W, Pang S F. Gynecol Obstet Invest., 1998; 45(4):247-52.
13. Cioni et al., Prenat Diagn. 2005; 25/3(198-202).
14. Bussani C. et al, Mol Diagn Ther. 2007.
15. Florio et al., Fertil Steril. 2010.
16. Hannan N J, et al. Reprod Sci. 2012; 19:1125-32.
17. Giulini S. et al. Arch Gynecol Obstet. 2012; 285:1479-1482.
18. Berlanga S. et al., Placenta 2011; 32 Suppl. 3:S271-5.
19. Ubaldi F, Bourgain C, Tournaye H, Smitz J, Steirteghem A, Devroey P. Fertil Steril, March 1997 67, 3: 521-526.
20. Schaeffer H J, Sirotkin A V. Adv Exp Med Biol. 1995; 395:547-548.
21. Kuramoto H, et al. Am. J. Obstet. Gynecol. 114: 1012-1019, 1972.
22. Mo B. et al, 2006) Mo B, Vendrov A E, Palomino W A, DuPont B R, Apparao K B, Lessey B A. Biol Reprod. 2006; 75(3):387-94.

23. Italiano D., Lena A M, Melino G, Candi E. Cell Cycle. 2012; 11(24):4589-96.
24. Duan W., et al. PLoS One. 2013; 8(3) Epub 6 Marzo 2013.

The invention claimed is:

1. An intrauterine gel composition comprising an effective amount of an active ingredient selected from N-acetyl-5-methoxy tryptamine, an analogue thereof, and a combination of N-acetyl-5-methoxy tryptamine and an analogue thereof, and further comprising one or more physiologically acceptable excipients or adjuvants, wherein the active ingredient is formulated as an endometrial irrigation or uterine washing or endometrial washing in a medium for cell culture at a final concentration ranging from $4\times10{-9}$ g/ml to $25\times10{-9}$ g/ml.

2. The composition of claim 1, wherein the gel composition is a controlled release gel composition.

3. The composition of claim 2, wherein the active ingredient is present in a concentration ranging from $10\times10^{-9}$ g/ml to $25\times10^{-9}$ g/ml.

4. The composition of claim 1, further comprising essential and non-essential amino acids and buffer salts, wherein the composition has a pH between 7-8.

5. A medical device for uterine washing comprising a sterile container comprising the composition of claim 1.

6. The medical device of claim 5, wherein the sterile container is disposable.

* * * * *